United States Patent
Gupta et al.

(10) Patent No.: US 9,873,908 B2
(45) Date of Patent: Jan. 23, 2018

(54) METHODS FOR THE ENRICHMENT OF MUTATED NUCLEIC ACID FROM A MIXTURE

(71) Applicant: Roche Molecular Systems, Inc., Pleasanton, CA (US)

(72) Inventors: Amar Gupta, Danville, CA (US); Nancy Schoenbrunner, Moraga, CA (US); Kevin Janssen, Philadelphia, PA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 247 days.

(21) Appl. No.: 14/547,899

(22) Filed: Nov. 19, 2014

(65) Prior Publication Data

US 2015/0147760 A1    May 28, 2015

Related U.S. Application Data

(60) Provisional application No. 61/909,587, filed on Nov. 27, 2013.

(51) Int. Cl.
    *C12Q 1/68* (2006.01)
(52) U.S. Cl.
    CPC ......... *C12Q 1/6806* (2013.01); *C12Q 1/6827* (2013.01)
(58) Field of Classification Search
    None
    See application file for complete search history.

(56) References Cited

U.S. PATENT DOCUMENTS

| | | | |
|---|---|---|---|
| 6,031,098 A | 2/2000 | Barton et al. | |
| 6,120,992 A * | 9/2000 | Wagner, Jr. .......... | C12Q 1/6827 435/6.11 |
| 6,306,601 B1 | 10/2001 | Barton et al. | |
| 6,444,661 B1 | 9/2002 | Barton et al. | |
| 6,630,301 B1 | 10/2003 | Gocke et al. | |
| 6,777,405 B2 | 8/2004 | Barton et al. | |
| 7,094,543 B2 | 8/2006 | Li-Sucholeiki et al. | |
| 7,345,172 B2 | 3/2008 | Barton et al. | |
| 7,935,484 B2 | 5/2011 | Gocke et al. | |
| 8,053,188 B2 | 11/2011 | Gullberg et al. | |
| 8,076,082 B2 | 12/2011 | Guo | |
| 2003/0082537 A1 * | 5/2003 | Stanton, Jr. .......... | C12Q 1/6876 435/6.11 |
| 2005/0148772 A1 * | 7/2005 | Barton ............... | A61K 41/0042 544/225 |
| 2007/0275386 A1 * | 11/2007 | Ratain .................. | C12Q 1/6886 435/6.14 |
| 2011/0003282 A1 | 1/2011 | Wain-Hobson et al. | |
| 2011/0217714 A1 | 9/2011 | Makrigiorgos | |
| 2012/0164641 A1 | 6/2012 | Bauer et al. | |

FOREIGN PATENT DOCUMENTS

| WO | 200105800 A2 | 1/2001 |
|---|---|---|
| WO | 200105800 A3 | 1/2001 |
| WO | 2001005800 A2 | 1/2001 |
| WO | 2002086169 A1 | 10/2002 |
| WO | 2007084380 A2 | 7/2007 |
| WO | 2007084380 A3 | 7/2007 |
| WO | PCT/EP2014/075460 | 2/2015 |

OTHER PUBLICATIONS

Asano, H. et al., Clin. Cancer Res. 2006, 12(1): 43-48; Detection of EGFR gene mutation in lung cancer by mutant-enriched polymerase chain reaction assay.
Benesova L. et al., Analytical Biochemistry 2013, 433(2):227-34; Mutation-based detection and monitoring of cell-free tumor DNA in peripheral blood of cancer patients.
Boon, E.M et al., Methods in Enzymology 2002, 353:506-522; Detection of DNA base mismatches using DNA intercalators.
Jackson, B.A. & Barton, J.K., Biochemistry 2000, 39: 6176-6182; Recognition of base mismatches in DNA by 5,6-chrysenequinone diimine complexes of rhodium(III): a proposed mechanism for preferential binding in destabilized regions of the double helix.
Li, J. et al., Nature Medicine 2008, 14(5): 579-584; Replacing PCR with COLD-PCR enriches variant DNA sequences and redefines the sensitivity of genetic testing.
Milbury, C.A. et al., Clinical Chemistry 2009, 55(4): 632-640; PCR-based methods for the enrichment of minority alleles and mutations.
Nollau, P. et al., Int. J. Cancer 1996, 66: 332-336; Detection of K-ras mutations in stools of patients with colorectal cancer by mutant-enriched PCR.
Zeglis, B.M. & Barton, J.K.. Nature Protocols 2007, 2(2): 357-371.

* cited by examiner

*Primary Examiner* — Amanda Haney
(74) *Attorney, Agent, or Firm* — David J. Chang

(57) ABSTRACT

The detection of the presence of rare somatic mutations from a biological sample is often challenging due to the simultaneous presence of a vast excess of wild-type DNA. The present invention describes methods that would allow the enrichment of mutant DNA by depleting amplifiable wild-type DNA.

9 Claims, 2 Drawing Sheets

US 9,873,908 B2

METHODS FOR THE ENRICHMENT OF MUTATED NUCLEIC ACID FROM A MIXTURE

CROSS REFERENCE TO RELATED INVENTION

This application claims the benefit of priority of U.S. Provisional Patent Application Ser. No. 61/909,587, filed Nov. 27, 2013, which is incorporated herein by reference in its entirety.

REFERENCE TO SEQUENCE LISTING

This application contains a Sequence Listing submitted as an electronic text file named "31873_US1.txt", having a size in bytes of 2 kb, and created on Oct. 13, 2014. The information contained in this electronic file is hereby incorporated by reference in its entirety pursuant to 37 CFR §1.52(e)(5).

FIELD OF THE INVENTION

The invention pertains to the fields of nucleic acid chemistry and nucleic acid amplification. In particular, the invention pertains to the enrichment of low abundance mutant target nucleic acids using compounds and methods that can detect base pair mismatches in nucleic acids.

BACKGROUND OF THE INVENTION

Most human inherited diseases and cancers are known to be caused by mutations in nuclear genes. In general, a mutation is considered to be particular polymorphic variants at a genetic locus. The mutation can be a single nucleotide difference, often referred to as a point mutation. At the cellular and tissue level, polymorphisms at a specific genetic locus may give rise to significantly altered cellular behavior. However, because even relatively small cell or tissue samples can contain millions or billions of DNA molecules containing the particular genetic locus, a representation of the range and frequencies of polymorphic variants at a genetic locus, requires detecting alleles that are potentially present at a very low frequency. In most cases, the detection of the presence of rare mutations from a biological sample presents tremendous challenges due to the simultaneous presence of a vast excess of wild-type DNA.

Thus there exists a need in the art for a method to selectively and accurately enrich low-copy mutant DNA such that their presence can be detectable following the performance of amplification reactions such as PCR.

SUMMARY OF THE INVENTION

The present invention is directed to methods for enriching low abundance alleles (e.g. mutant DNA) in a sample that allows subsequent detection of such alleles. In a first aspect, the invention relates to a method of enriching a variant of a target nucleic acid in a mixture of nucleic acids from a sample, the target nucleic acid existing in the form of two variant sequences, wherein said variants differ at a single nucleotide position, the method comprising, providing the sample that includes the target nucleic acid wherein the variant to be enriched is present in the sample in low abundance amongst a large excess of the other variant; providing an oligonucleotide that is complementary to one strand of the target nucleic acid at a concentration that is in molar excess to the target nucleic acid, wherein the oligonucleotide is attached with an affinity label and is perfectly matched at the single nucleotide position with the variant to be enriched and has a mismatch at the single nucleotide position with the other variant; providing conditions suitable for hybridization of the oligonucleotide to the target nucleic acid to generate duplex polynucleotides consisting of the oligonucleotide and one strand of either variant of the target nucleic acid; contacting the duplex polynucleotides with a mismatch intercalating compound that preferentially binds to only the duplex polynucleotides that contain a mismatch wherein said compound is further capable of catalyzing cleavage of one strand of the duplex polynucleotide at the mismatch site with light; subjecting the duplex polynucleotides to light resulting in both cleaved and uncleaved duplex polynucleotides; applying both cleaved and uncleaved duplex polynucleotides to an affinity matrix that recognizes and binds to the affinity label on the oligonucleotide; providing conditions whereby only the cleaved duplex polynucleotide is denatured and removing the denatured single strand from the affinity matrix; and providing a buffer under conditions to denature the uncleaved polynucleotide duplex; and collecting the buffer which contains one strand of the enriched variant of the target nucleic acid. In one embodiment, the mismatch intercalating compound is $Rh(bpy)_2(chrysi)^{3+}$ or $Rh(bpy)_2(phzi)^{3+}$ or their respective analogs. In another embodiment, the invention relates to a further step of amplifying and detecting the enriched variant of the target nucleic acid.

In a second aspect, the invention relates to a method for detecting a mutant allele of a target nucleic acid in a mixture of nucleic acids from a sample wherein the mutant allele differs from a wild-type allele at a single nucleotide position and is present in the sample in low abundance amongst a large excess of the wild-type allele, the method comprising enriching the mutant allele in the sample wherein the enrichment is performed by providing an oligonucleotide that is complementary to one strand of the target nucleic acid at a concentration that is in molar excess to the target nucleic acid, wherein the oligonucleotide is attached with an affinity label and is perfectly matched at the single nucleotide position with the mutant allele and has a mismatch at the single nucleotide position with the wild-type allele; providing conditions suitable for hybridization of the oligonucleotide to the target nucleic acid to generate duplex polynucleotides consisting of the oligonucleotide and one strand of either the mutant allele or the wild-type allele; contacting the duplex polynucleotides with a mismatch intercalating compound that preferentially binds to only the duplex polynucleotides that contain a mismatch wherein said compound is further capable of catalyzing cleavage of one strand of the duplex polynucleotide at the mismatch site with light; subjecting the duplex polynucleotides to light resulting in both cleaved and uncleaved duplex polynucleotides; applying both cleaved and uncleaved duplex polynucleotides to an affinity matrix that recognizes and binds to the affinity label on the oligonucleotide; providing conditions whereby only the cleaved duplex polynucleotide is denatured and removing the denatured single strand of the wild-type allele from the affinity matrix; providing a buffer under conditions to denature the uncleaved polynucleotide duplex; and collecting the buffer which contains one strand of the enriched mutant allele of the target nucleic acid; amplifying the enriched mutant allele; and detecting the product of the enriched amplified mutant allele or the signal generated from the enriched amplified mutant allele. In one embodiment, the mismatch intercalating compound is Rh(bpy)$_2$(chrysi)$^{3+}$ or Rh(bpy)$_2$(phzi)$^{3+}$ or their respective analogs.

DETAILED DESCRIPTION OF THE INVENTION

Definitions

Figure 1:
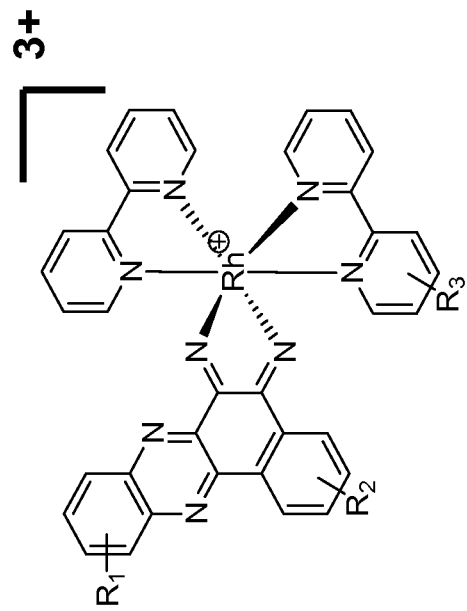
FIG. 1 shows the structures of the rhodium-based intercalators, Rh(bpy)$_2$(chrysi)$^{3+}$ (left) and Rh(bpy)$_2$(phzi)$^{3+}$ (right), where N represents nitrogen, Rh represents rhodium, and R$_1$, R$_2$ and R$_3$ are independently selected from the group consisting of hydrogen, alkyl, aryl, a solid support, and a linker attached with an affinity label.
Figure 1:
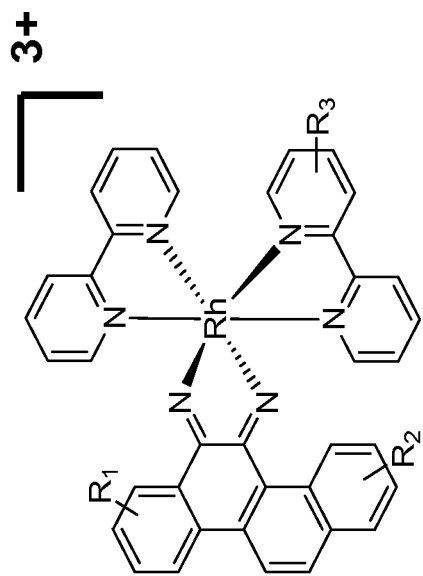

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd ed. 1994); *The Cambridge Dictionary of Science and Technology* (Walker ed., 1988); *The Glossary of Genetics*, 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

The term "nucleic acid" refers to polymers of nucleotides (e.g., ribonucleotides, deoxyribonucleotides, nucleotide analogs etc.) and comprising deoxyribonucleic acids (DNA), ribonucleic acids (RNA), DNA-RNA hybrids, oligonucleotides, polynucleotides, aptamers, peptide nucleic acids (PNAs), PNA-DNA conjugates, PNA-RNA conjugates, etc., that comprise nucleotides covalently linked together, either in a linear or branched fashion. A nucleic acid is typically single-stranded or double-stranded and will generally contain phosphodiester bonds, although in some cases, nucleic acid analogs are included that may have alternate backbones, including, for example, phosphoramide (Beaucage et al. (1993) Tetrahedron 49(10):1925); phosphorothioate (Mag et al. (1991) Nucleic Acids Res. 19:1437; and U.S. Pat. No. 5,644,048), phosphorodithioate (Briu et al. (1989) J. Am. Chem. Soc. 111:2321), O-methylphophoroamidite linkages (see Eckstein, Oligonucleotides and Analogues: A Practical Approach, Oxford University Press (1992)), and peptide nucleic acid backbones and linkages (see, Egholm (1992) J. Am. Chem. Soc. 114:1895). Other analog nucleic acids include those with positively charged backbones (Denpcy et al. (1995) Proc. Natl. Acad. Sci. USA 92: 6097); non-ionic backbones (U.S. Pat. Nos. 5,386,023, 5,637,684, 5,602,240, 5,216,141 and 4,469,863) and non-ribose backbones, including those described in U.S. Pat. Nos. 5,235,033 and 5,034,506. Nucleic acids containing one or more carbocyclic sugars are also included within the definition of nucleic acids (see Jenkins et al. (1995) Chem. Soc. Rev. pp. 169-176), and analogs are also described in, e.g., Rawls, C & E News Jun. 2, 1997 page 35. These modifications of the ribose-phosphate backbone may be done to facilitate the addition of additional moieties such as labels, or to alter the stability and half-life of such molecules in physiological environments.

In addition to the naturally occurring heterocyclic bases that are typically found in nucleic acids (e.g., adenine, guanine, thymine, cytosine, and uracil), nucleotide analogs also may include non-naturally occurring heterocyclic bases, such as those described in, e.g., Seela et al. (1999) Helv. Chim. Acta 82:1640. Certain bases used in nucleotide analogs act as melting temperature (Tm) modifiers. For example, some of these include 7-deazapurines (e.g., 7-deazaguanine, 7-deazaadenine, etc.), pyrazolo[3,4-d]pyrimidines, propynyl-dN (e.g., propynyl-dU, propynyl-dC, etc.), and the like. See, e.g., U.S. Pat. No. 5,990,303, which is incorporated herein by reference. Other representative heterocyclic bases include, e.g., hypoxanthine, inosine, xanthine; 8-aza derivatives of 2-aminopurine, 2,6-diaminopurine, 2-amino-6-chloropurine, hypoxanthine, inosine and xanthine; 7-deaza-8-aza derivatives of adenine, guanine, 2-aminopurine, 2,6-diaminopurine, 2-amino-6-chloropurine, hypoxanthine, inosine and xanthine; 6-azacytidine; 5-fluorocytidine; 5-chlorocytidine; 5-iodocytidine; 5-bromocytidine; 5-methylcytidine; 5-propynylcytidine; 5-bromovinyluracil; 5-fluorouracil; 5-chlorouracil; 5-iodouracil; 5-bromouracil; 5-trifluoromethyluracil; 5-methoxymethyluracil; 5-ethynyluracil; 5-propynyluracil, and the like.

A "nucleoside" refers to a nucleic acid component that comprises a base or basic group (comprising at least one homocyclic ring, at least one heterocyclic ring, at least one aryl group, and/or the like) covalently linked to a sugar moiety (a ribose sugar or a deoxyribose sugar), a derivative of a sugar moiety, or a functional equivalent of a sugar moiety (e.g. a carbocyclic ring). For example, when a nucleoside includes a sugar moiety, the base is typically linked to a 1'-position of that sugar moiety. As described above, a base can be a naturally occurring base or a non-naturally occurring base. Exemplary nucleosides include ribonucleosides, deoxyribonucleosides, dideoxyribonucleosides and carbocyclic nucleosides.

A "nucleotide" refers to an ester of a nucleoside, e.g., a phosphate ester of a nucleoside, having one, two, three or more phosphate groups covalently linked to a 5' position of a sugar moiety of the nucleoside.

The terms "polynucleotide" and "oligonucleotide" are used interchangeably. "Oligonucleotide" is a term sometimes used to describe a shorter polynucleotide. An oligonucleotide may be comprised of at least 6 nucleotides, for example at least about 10-12 nucleotides, or at least about 15-30 nucleotides corresponding to a region of the designated nucleotide sequence.

The term "enriching a variant of a target nucleic acid sequence" refers to increasing the amount of the desired variant of the target nucleic acid sequence and increasing the ratio of the desired variant relative to the undesired variant in a sample. Generally, the desired variant to be enriched is less prevalent in a nucleic acid sample than the undesired variant, and makes up less than 50% of the total amount of all the variants of the target nucleic acid sequence. In many cases, the desired variant refers to a mutant allele and the undesired variant refers to a wild-type allele.

The term "wild-type" as used herein refers to a gene or allele which has the characteristics of that gene or allele when isolated from a naturally occurring source. A wild-type gene or a wild-type allele is that which is most frequently observed in a population and is arbitrarily designated as the "normal" or "wild-type" form of the gene or allele.

In contrast, the term "mutant" or "mutated" refers to a gene or allele which displays modifications in sequence when compared to the wild-type gene or allele. The term "mutation" refers to a change in the sequence of nucleotides of a normally conserved nucleic acid sequence resulting in the formation of a mutant as differentiated from the normal (unaltered) or wild type sequence. Mutations can generally be divided into two general classes, namely, base-pair substitutions (e.g. single nucleotide substitutions) and frameshift mutations. The latter entail the insertion or deletion of one to several nucleotide pairs.

The term "allele" refers to two sequences which are different by only one or a few bases.

The term "mismatch" DNA or "heteroduplex" DNA refers to DNA which includes one or more mismatch base pairings. A mismatch base pairing refers to a specific pair of opposing bases, in the context of a DNA duplex, which cannot form one of the hydrogen-bonded base pairs, T with A or G with C. Heteroduplex DNA includes double-stranded DNA in which one or more bases in one strand does or do not complement the base or bases in the opposing strand, as well as double-stranded DNA in which one or more bases of either strand does or do not have an opposing base, due to an insertion or deletion in one strand as compared to the opposing strand. In contrast, homoduplex DNA refers to double-stranded DNA in which each strand is a complete complement of the other strand, and each base forms a hydrogen-bonded base pair with an opposing base.

The terms "molecular binding partners" and "specific binding partners" refer to pairs of molecules, typically pairs of biomolecules, that exhibit specific binding. Non-limiting examples are receptor and ligand, antibody and antigen, biotin and avidin, and biotin and streptavidin. Molecular binding partners can also be represented by binding that occurs between an "affinity label" and an "affinity matrix" as defined below.

An "affinity" label is a molecule that can specifically bind to its molecular binding partner. The binding can be through covalent or non-covalent (e.g., ionic, hydrogen, etc.) bonds. As used herein, an affinity label, such as biotin, can selectively bind to an affinity matrix, such as streptavidin-coated beads or particles. An affinity label can be attached to an oligonucleotide on its 3' terminus, 5' terminus or on an internal position of the oligonucleotide.

An "affinity matrix" as used herein refers to a molecule that is attached to the surface of a solid support or solid matrix (e.g. magnetic latex particles, glass beads) that can specifically bind to its molecular binding partner. The binding can be through covalent or non-covalent bonds. As used herein, an affinity matrix, such as streptavidin-coated magnetic latex particles can selectively bind to an affinity label, such as biotin.

An "alkyl group" refers to a linear, branched, or cyclic saturated hydrocarbon moiety and includes all positional isomers, e.g., methyl, ethyl, propyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, n-hexyl, cyclohexyl, n-heptyl, n-octyl, 2-ethylhexyl, n-nonyl, n-decyl and the like. An alkyl group typically comprises about 1-20 carbon atoms and more typically comprises about 2-15 carbon atoms. Alkyl groups can be substituted or unsubstituted.

An "aryl group" refers to a substituent group of atoms or moiety that is derived from an aromatic compound. Exemplary aryl groups include, e.g., phenyl groups, or the like. Aryl groups optionally include multiple aromatic rings (e.g., diphenyl groups, etc.). In addition, an aryl group can be substituted or unsubstituted.

"PCR amplification" or simply "PCR" refers to the polymerase chain reaction that involves the use of a nucleic acid sequence as a template for producing a large number of complements to that sequence. The template may be hybridized to a primer having a sequence complementary to a portion of the template sequence and contacted with a suitable reaction mixture including dNTPs and a polymerase enzyme. The primer is elongated by the polymerase enzyme producing a nucleic acid complementary to the original template. For the amplification of both strands of a double stranded nucleic acid molecule, two primers are used, each of which may have a sequence which is complementary to a portion of one of the nucleic acid strands. The strands of the nucleic acid molecules are denatured, for example by heating, and the process is repeated, this time with the newly synthesized strands of the preceding step serving as templates in the subsequent steps. A PCR amplification protocol may involve a few to many cycles of denaturation, hybridization and elongation reactions to produce sufficient amounts of the target nucleic acid.

The term "allele-specific primer" or "AS primer" refers to a primer that hybridizes to more than one variant of the target sequence, but is capable of discriminating between the variants of the target sequence in that only with one of the variants, the primer is efficiently extended by the nucleic acid polymerase under suitable conditions. With other variants of the target sequence, the extension is less efficient, inefficient or undetectable.

The term "common primer" refers to the second primer in the pair of primers that includes an allele-specific primer. The common primer is not allele-specific, i.e. does not discriminate between the variants of the target sequence between which the allele-specific primer discriminates.

The terms "complementary" or "complementarity" are used in reference to antiparallel strands of polynucleotides related by the Watson-Crick base-pairing rules. The terms "perfectly complementary" or "100% complementary" refer to complementary sequences that have Watson-Crick pairing of all the bases between the antiparallel strands, i.e. there are no mismatches between any two bases in the polynucleotide duplex. However, duplexes are formed between antiparallel strands even in the absence of perfect complementarity. The terms "partially complementary" or "incompletely complementary" refer to any alignment of bases between antiparallel polynucleotide strands that is less than 100% perfect (e.g., there exists at least one mismatch or unmatched base in the polynucleotide duplex). The duplexes between partially complementary strands are generally less stable than the duplexes between perfectly complementary strands.

The term "sample" refers to any composition containing or presumed to contain nucleic acid. This includes a sample of tissue or fluid isolated from an individual for example, skin, plasma, serum, spinal fluid, lymph fluid, synovial fluid, urine, tears, blood cells, organs and tumors, and also to samples of in vitro cultures established from cells taken from an individual, including the formalin-fixed paraffin embedded tissues (FFPET) and nucleic acids isolated therefrom.

The term "primary sequence" refers to the sequence of nucleotides in a polynucleotide or oligonucleotide. Nucleotide modifications such as nitrogenous base modifications, sugar modifications or other backbone modifications are not a part of the primary sequence. Labels, such as chromophores conjugated to the oligonucleotides are also not a part of the primary sequence. Thus two oligonucleotides can share the same primary sequence but differ with respect to the modifications and labels.

The term "primer" refers to an oligonucleotide which hybridizes with a sequence in the target nucleic acid and is capable of acting as a point of initiation of synthesis along a complementary strand of nucleic acid under conditions suitable for such synthesis. As used herein, the term "probe" refers to an oligonucleotide which hybridizes with a sequence in the target nucleic acid and is usually detectably labeled. The probe can have modifications, such as a 3'-terminus modification that makes the probe non-extendable by nucleic acid polymerases, and one or more chromophores. An oligonucleotide with the same sequence may serve as a primer in one assay and a probe in a different assay.

As used herein, the term "target sequence", "target nucleic acid" or "target" refers to a portion of the nucleic acid sequence which is to be either amplified, detected or both.

The terms "hybridized" and "hybridization" refer to the base-pairing interaction of between two nucleic acids which results in formation of a duplex. It is not a requirement that two nucleic acids have 100% complementarity over their full length to achieve hybridization.

The terms "selective hybridization" and "specific hybridization" refer to the hybridization of a nucleic acid predominantly (50% or more of the hybridizing molecule) or nearly exclusively (90% or more of the hybridizing molecule) to a particular nucleic acid present in a complex mixture where other nucleic acids are also present. For example, under typical PCR conditions, primers specifically hybridize to the target nucleic acids to the exclusion of non-target nucleic acids also present in the solution. The specifically hybridized primers drive amplification of the target nucleic acid to produce an amplification product of the target nucleic acid that is at least the most predominant amplification product and is preferably the nearly exclusive (e.g., representing 90% or more of all amplification products in the sample) amplification product. Preferably, the non-specific amplification product is present in such small amounts that it is either non-detectable or is detected in such small amounts as to be easily distinguishable from the specific amplification product. Similarly, probes specifically hybridize to the target nucleic acids to the exclusion of non-target nucleic acids also present in the reaction mixture. The specifically hybridized probes allow specific detection of the target nucleic acid to generate a detectable signal that is at least the most predominant signal and is preferably the nearly exclusive (e.g., representing 90% or more of all amplification products in the sample) signal.

There is a continuing need for developing new methods that can detect rare somatic mutations associated with various types of cancer with increased accuracy and sensitivity. A particular need for more sensitive detection methods exists in the field of cancer biomarker detection from peripheral fluids such as blood, sputum, and urine. During the past several years, many studies have been published, that have clearly established the value of blood-based cancer biomarker detection for therapy prediction, therapeutic monitoring of drug resistance development, and tumor dynamics and cancer recurrence by monitoring defined mutations in blood. Furthermore, a highly sensitive method for mutation detection from peripheral biological fluids may someday deliver on the promise of a "liquid biopsy" approach for cancer screening and early stage cancer detection.

Many methods have been developed over the years to increase the sensitivity of rare mutation detection. Most of the methods have generally focused on capitalizing on the sequence based differences between mutant and wild-type, by employing primer- or probe-based discrimination during PCR, commonly referred as allele-specific PCR (AS-PCR). These methods are successful down to a level of 0.1-1% mutant levels, but then further improvements are limited by enzyme based limitations or PCR errors. Digital PCR, pioneered by Bert Vogelstein, to date has been the most promising technique to successfully enhance the sensitivity of rare allele detection. This is accomplished by dividing the sample into thousands of smaller amplification reactions. This method, in effect, dilutes out the wild-type DNA, and enriches the ratio of mutant to wild-type. An alternative approach proposed presently is to use an upfront sample preparation method that enriches the mutant DNA, and thereby reduces the difficulty of detection in the downstream assay.

PCR, in its many different modalities, is a powerful technique that can readily detect literally a single copy of a specific sequence in the presence of a large amount of background DNA, provided that the nature of the desired sequence is sufficiently different from the background DNA. This is the case for example, when trying to detect the presence of an exogenous pathogenic sequence from a biological specimen also containing an excess of human genomic DNA. However, the problem becomes increasingly challenging when the sequence of interest becomes increasingly similar to the sequences present in the background DNA, as is the case in the detection of rare somatic mutations. Generally, the mutation status must be determined in a sample that also contains a large excess of the wild type sequence. This is challenging because although the currently available methods for mutation detection are selective for the mutant sequence, they are not absolute in specificity, and as the ratio of wild-type to mutant increases, it becomes increasingly difficult to distinguish mutant from wild-type DNA.

The methods described in the present invention are based on the use of bulky rhodium (III) complexes as disclosed in U.S. Pat. No. 6,031,098, U.S. Pat. No. 6,306,601, Nature Protocols 2: 357-371, 2007 (each of which are incorporated by reference herein), where Barton et al. describe the synthesis and function of two families of mismatch-specific rhodium-based intercalators based on a pair of bulky intercalating ligands, 5,6-chrysenequinone diimine (chrysi) and 3,4-benzo[a]phenazine quinone diimine (phzi) to generate, respectively, $Rh(bpy)_2(chrysi)^{3+}$ or $Rh(bpy)_2(phzi)^{3+}$. These compounds are known for their ability to insert themselves selectively into the bulge created by a nucleotide mismatch within a DNA duplex. The mechanism of binding has been evaluated by multiple NMR and crystallography based investigations, and the results have been remarkable. Unlike the classical intercalative binding mode where the binder enters the DNA duplex from the major groove, and intercalates between base pairs, these novel compounds enter the minor groove of the DNA, insert the bulky aromatic ligand, and eject the mismatched bases into the major groove. Upon photoactivation, the complex promotes direct strand scission at single-base mismatch sites within the duplex. Site-specific cleavage is evident at nanomolar concentrations. The main focus so far on the use of these rhodium compounds has been in the detection of single-nucleotide polymorphisms (SNPs), and novel chemotherapeutics (Boon, E M et al., Methods in Enzymology, 353:506-522, 2002, U.S. Pat. No. 6,444,661, U.S. Pat. No. 6,777,405, each of which are incorporated by reference herein).

In the present invention, these rhodium compounds have been applied for the purpose of the enrichment of rare alleles (e.g. rare mutant alleles). The structures of the compounds chosen for this study are shown in FIG. 1, where R1, R2, R3 can be H, alkyl, aryl, or a solid phase, or linker with an affinity label (e.g. biotin). Although it has previously been shown that the described compounds can bind to mismatched DNA duplexes and catalyze photocleavage, it has also been shown that the photocleavage only results in the cleavage of only one of the two strands. This is of little utility in the enrichment application of mutant DNA because an uncleaved wild-type strand would still be present and can function as a template for amplification.

Figure 2:
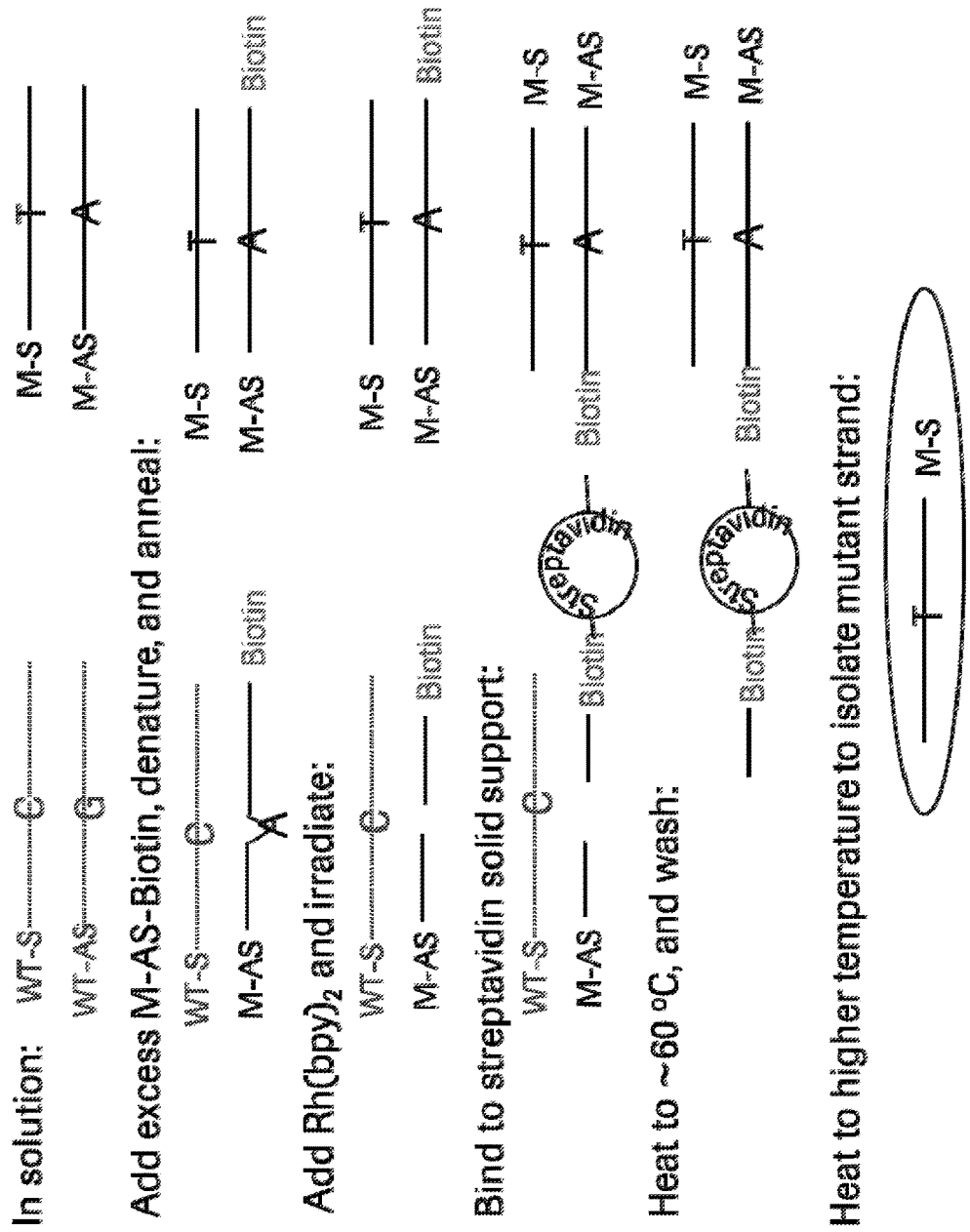
FIG. 2 shows a graphical representation of the method of the present invention for the enrichment of a single strand of the mutant allele.

The overall strategy of the present invention is graphically represented on FIG. 2 and takes advantage of the ability of these rhodium complex compounds to bind to base mismatched region of interest, and cause the cleavage of a specific phosphodiester linkage upon photoactivation. According to the methods described here, a sample is provided in which the target nucleic acid contains both the wild-type allele (shown in FIG. 2 as having a "C" nucleotide on the sense strand, "WT-S" and "G" nucleotide on the antisense strand "WT-AS" and the mutant allele (shown as having a "T" nucleotide on the sense strand "M-S" and a "A" nucleotide on the antisense strand, "M-AS").

Next, a single-stranded oligonucleotide (represented in FIG. 2 as M-AS-Biotin) corresponding to one strand of the mutant allele desired to be enriched and comprising an affinity ligand (e.g. biotin) is offered in excess relative to amount of the target nucleic acid in the sample. (Although FIG. 2 shows the oligonucleotide corresponding to the antisense strand with the biotin label on its 3' terminus, the method could also be practiced with an oligonucleotide having the sequence of the sense strand of the mutant allele with the biotin label attached at any position other than mutation site.) Then the mixture is first heated in order to denature all double-stranded sample DNA and then cooled to allow annealing of complementary single strands. Because the M-AS-Biotin oligonucleotide is present in excess, almost all of the sense strand of the target nucleic acid (both the wild-type allele, WT-S and the mutant allele, M-S) will be hybridized to the oligonucleotide. While the mutant sense strand duplexes will be perfectly matched, the wild-type sense strand will have a single base mismatch at the position of mutation.

The rhodium complex compound (represented in FIG. 2 as "Rh(bpy)$_2$") is then added to the mixture. Upon photo-activation, the mismatch-containing duplex will be cleaved, either on the M-AS-Biotin oligonucleotide (as shown in FIG. 2) or on the wild-type sense strand, WT-S, while the duplexes with the M-AS-Biotin oligonucleotide bound to the mutant sense strand, M-S, will not be cleaved due to a perfect match at the mutation position. Using the affinity portion (shown as Biotin in FIG. 2) of the oligonucleotide, all the oligonucleotide bound sequences (i.e. wild-type and mutant sense strands) are captured on a solid phase (shown in FIG. 2 as a streptavidin-coated solid support), and all the excess wild-type and mutant antisense strands are washed away. In the next step, the solid phase is placed in the appropriate buffer and the temperature is raised until only the captured wild-type sense strand is released due to the lower melting temperature of the cleavage-containing duplex. This is then washed away, leaving only the mutant sense strand on the support. Finally the mutant sense strand is recovered in buffer by either a temperature or alkaline pH elution step.

While FIG. 2 shows the use of an antisense strand oligonucleotide for the enrichment of the mutant sense strand, similarly a sense strand oligonucleotide can be used for the enrichment of the mutant antisense strand. Generally, the choice for which strand to use for the oligonucleotide depends on the binding affinity of the rhodium complex compound to the mismatch position, with the most thermodynamically destabilized mismatch sites having the highest binding affinities (for further details, see Jackson, B. A. and Barton, J. K., Biochemistry 39: 6176-6182, 2000, which is incorporated by reference herein).

The following examples and figures are provided to aid the understanding of the present invention, the true scope of which is set forth in the appended claims. It is understood that modifications can be made in the procedures set forth without departing from the spirit of the invention.

EXAMPLES

Example 1 Control Experiment Using Single Stranded Oligonucleotides

The following experiment is used to enrich a sense-strand mutant (MU-S) oligonucleotide in the presence of a sense-strand wild-type (WT-S) oligonucleotide by using an affinity-labeled anti-sense strand (AL-AS) oligonucleotide that is perfectly matched to the mutant oligonucleotide and has a one-base mismatch with the wild-type oligonucleotide. The sequences of the oligonucleotides are as follows (mismatch site bolded):

```
WT-S:
                                        (SEQ ID NO: 1)
5'-CGTGCAGCTCATCACGCAGCTCATGCCCTT-3'

MU-S:
                                        (SEQ ID NO: 2)
5'-CGTGCAGCTCATCATGCAGCTCATGCCCTT-3'

AL-AS:
                                        (SEQ ID NO: 3)
5'-AAGGGCATGAGCTGCATGATGAGCTGCACG-Biotin-3'
```

A reaction mixture is prepared with 10 µl 150 mM Glycine, pH 9.5, 2 µl 5M NaCl and 55 µl water. To this solution is added 10 µl of 10 µM WT-S, 10 µl of 10 µM MU-S, and 10 µl of 50 µM AL-AS and 3 µl of 100 µM Rh(bpy)$_2$(phzi)$^{3+}$. The solution is vortexed and incubated at room temperature for 5 minutes. (Final concentrations: 15 µM Glycine pH 9.5, 100 µM NaCl, 1 µM WT-S, 1 µM MU-S, 5 µM AL-AS, and 3 µM Rh(bpy)$_2$phzi$^{3+}$). The reaction mixture is then irradiated in a Stratagene UV Stratalinker 1800 using 365 nm bulbs for 30 minutes to cleave one strand of the sense-antisense duplex that contains the mismatch.

A separate solution of 25 µL of 10 mg/mL Solulink streptavidin magnetic beads is washed with 1 mL of 15 µM Glycine pH 9.5 buffer and the beads are separated from the supernatant using a magnet. The reaction mixture with the cleaved and uncleaved oligonucleotide duplexes is added to the magnetic bead pellet and mixed. The resulting mixture is incubated at room temperature for 30 minutes. Afterwards, the solution is heated to 60° C. or to the determined melting temperature of the uncleaved WT-S strand bound to the cleaved AL-AS strand (or of the cleaved WT-S strand bound to the uncleaved AL-AS strand), magnetically separated, and the supernatant is removed, such that only the uncleaved MU-S strand is still bound to the uncleaved AL-AS strand on the magnetic bead. The MU-S strand is removed by treating the magnetic beads with 100 µL of 20 µM NaOH, magnetically separating the solution, and decanting the supernatant into a test tube for further analysis.

Example 2 Control Experiment Using Double Stranded Oligonucleotides

The following experiment is used to enrich a sense-strand mutant (MU-S) oligonucleotide in the presence of a sense-strand wild-type (WT-S) oligonucleotide, an antisense-strand wild-type (WT-AS) oligonucleotide and an antisense-strand mutant (MU-AS) oligonucleotide by using an affinity-labeled anti-sense strand (AL-AS)oligonucleotide that has the identical sequence to the MU-AS oligonucleotide and has a one-base mismatch with the WT-AS oligonucleotide. The sequences of the oligonucleotides are as follows (mismatch site bolded):

```
WT-S:
                                       (SEQ ID NO: 1)
5'-CGTGCAGCTCATCACGCAGCTCATGCCCTT-3'

WT-AS:
                                       (SEQ ID NO: 4)
5'-AAGGGCATGAGCTGCGTGATGAGCTGCACG-3'

MU-S:
                                       (SEQ ID NO: 2)
5'-CGTGCAGCTCATCATGCAGCTCATGCCCTT-3'

MU-AS:
                                       (SEQ ID NO: 5)
5'-AAGGGCATGAGCTGCATGATGAGCTGCACG-3'

AL-AS:
                                       (SEQ ID NO: 3)
5'-AAGGGCATGAGCTGCATGATGAGCTGCACG-Biotin-3'
```

A reaction mixture is prepared with 10 µl 150 mM Glycine, pH 9.5 and 57 µl water. To this solution is added 10 µl of a mixture of 10 µM WT-S and WT-AS, 10 µl of a mixture of 10 µM MU-S and MU-AS, and 10 µl of 100 µM AL-AS. The resulting solution is incubated at 95° C. for 5 minutes to dissociate the double stranded oligonucleotides to single strands, and then the solution is cooled to room temperature to allow the single stranded oligonucleotides to re-anneal. 3 µL of 100 µM Rh(bpy)$_2$phzi$^{3+}$ is added to the solution, the solution is vortexed, and incubated at room temperature for 5 minutes. (Final concentrations: 15 µM Glycine pH 9.5, 1 µM WT-S, 1 µM WT-AS, 1 µM MU-S, 1 µM MU-AS, 10 µM AL-AS, and 3 µM Rh(bpy)$_2$phzi$^{3+}$). The reaction mixture is then irradiated in a Stratagene UV Stratalinker 1800 using 365 nm bulbs for 15 minutes to cleave one strand of the sense-antisense duplexes that contains the mismatch. The 10-fold concentration excess of the AL-AS oligonucleotide serves to increase the probability that most of the MU-S strand would bind to AL-AS rather than to the MU-AS strand.

A separate solution of 50 µL of 10 mg/mL Solulink streptavidin magnetic beads is washed with 1 mL of 15 µM Glycine pH 9.5 buffer and the beads are separated from the supernatant by using a magnet. The reaction mixture with cleaved and uncleaved oligonucleotide duplexes is added to the magnetic bead pellet and mixed. The resulting mixture is incubated at room temperature for 30 minutes. Afterwards, the solution is heated to 60° C. or to the determined melting temperature of the uncleaved WT-S strand bound to the cleaved AL-AS strand (or of the cleaved WT-S strand bound to the uncleaved AL-AS strand), magnetically separated. All WT-AS, MU-AS and WT-S strands are removed with the supernatant, such that only the uncleaved MU-S strand is still bound to the uncleaved AL-AS strand on the magnetic bead. The MU-S strand is removed by treating the magnetic beads with 100 µL of 20 µM NaOH, magnetically separating the solution, and decanting the supernatant into a test tube for further analysis.

Example 3 Enrichment and Detection of EGFR Mutant DNA

A sample is provided from which a mixture of nucleic acids, for example, human genomic DNA, can be extracted. The sample can be from a tissue such as skin, organs, and tumors or from fluid such as blood, plasma, serum, urine, or from any composition containing or presumed to contain nucleic acid. From this mixture of nucleic acids, a target gene of interest, for example, the human EGFR gene, may contain a certain variation such as a point mutation that is present in low abundance amongst a large excess of the other variant of the gene, which would be the non-mutant or wild-type gene. An example of an EGFR gene mutation that has clinical relevance to the development of cancer is the T790M mutation.

To enrich for the low-abundance T790M mutant allele of the EGFR gene, an excess of a biotin labeled antisense strand oligonucleotide (BL-AS) that is complementary to and perfectly matched with the sense strand of the T790M mutant allele is added to a solution containing the extracted genomic DNA. The solution is then heated at 90° C. or higher temperature to denature the double-stranded genomic DNA and then gradually cooled to a temperature to allow reannealing of the single DNA strands to occur. During the annealing step, the BL-AS strand can form duplexes with both the T790M mutant sense strand with which it is perfectly matched and also with the wild-type sense strand which will have a mismatch at the position of the point mutation.

The rhodium chelator, Rh(bpy)$_2$(phzi)$^{3+}$, is then added to the solution and allowed to incubate such that the chelator can bind only to the BL-AS: wild-type sense strand duplexes at the position of the mismatch. The reaction mixture is then irradiated in a Stratagene UV Stratalinker 1800 using 365 nm bulbs for 15 minutes to cleave one strand of BL-AS: wild-type sense strand duplexes. Next, a solid matrix coated with streptavidin is added. Examples of such solid matrices would be streptavidin coated magnetic particles such as Streptavidin-coupled Dynabeads® from Invitrogen, Streptavidin MagneSphere® Paramagnetic Particles from Promega, and NanoLink™ and MagnaLink™ Streptavidin Magnetic Beads from Solulink. Following incubation (e.g. 40° C. for 1 hour), a magnet is used to separate the particles and wash away all the nucleic acid that is not bound to the particles, which includes both mutant and wild-type antisense strands and any excess BL-AS. The wild-type sense strand (which is either cleaved at the mismatch site or is bound to a cleaved BL-AS oligonucleotide is then eluted from the magnetic particles using an appropriate elution buffer at a temperature that corresponds to the melting temperature of the mismatch duplex. As a result, only the T790M sense strand remains attached to the magnetic particles by being hybridized to the uncleaved biotin-labeled T790M antisense oligonucleotide. By then subjecting the particles to either high temperature or to alkaline pH conditions, the T790M sense strand can dissociate from the BL-AS oligonucleotide and collected for use in an amplification reaction for detection.

While the invention has been described in detail with reference to specific examples, it will be apparent to one skilled in the art that various modifications can be made within the scope of this invention. Thus the scope of the invention should not be limited by the examples described herein, but by the claims presented below.

The invention claimed is:

1. A method of enriching a variant of a target nucleic acid in a mixture of nucleic acids from a sample, the target nucleic acid existing in the form of two variant sequences, wherein said variants differ at a single nucleotide position, the method comprising:

providing the sample that includes the target nucleic acid wherein the variant to be enriched is present in the sample in low abundance amongst a large excess of the other variant;

providing an oligonucleotide that is complementary to one strand of the target nucleic acid at a concentration that is in molar excess to the target nucleic acid, wherein the oligonucleotide is attached with an affinity label and is perfectly matched at the single nucleotide position with the variant to be enriched and has a mismatch at the single nucleotide position with the other variant;

providing conditions suitable for hybridization of the oligonucleotide to the target nucleic acid to generate duplex polynucleotides consisting of the oligonucleotide and one strand of either variant of the target nucleic acid;

contacting the duplex polynucleotides with a mismatch intercalating compound that preferentially binds to only the duplex polynucleotides that contain a mismatch wherein said compound is further capable of catalyzing cleavage of one strand of the duplex polynucleotide at the mismatch site with light;

subjecting the duplex polynucleotides to light resulting in both cleaved and uncleaved duplex polynucleotides;

applying both cleaved and uncleaved duplex polynucleotides to an affinity matrix that recognizes and binds to the affinity label on the oligonucleotide;

providing conditions whereby only the cleaved duplex polynucleotide is denatured and removing the denatured single strand from the affinity matrix; and providing a buffer under conditions to denature the uncleaved polynucleotide duplex; and collecting the buffer which contains one strand of the enriched variant of the target nucleic acid.

2. The method of claim 1 wherein the mismatch intercalating compound is Rh(bpy)2(chrysi)3+, Rh(bpy)2(phzi)3+, or their analogs.

3. The method of claim 2 wherein the variant to be enriched is a mutant allele and the other variant is a wild-type allele.

4. The method of claim 3 wherein the mutant allele is a mutant EGFR allele and the wild-type allele is a wild-type EGFR allele.

5. The method of claim 3 or 4, further comprising a step of amplifying and detecting the mutant allele.

6. A method for detecting a mutant allele of a target nucleic acid in a mixture of nucleic acids from a sample wherein the mutant allele differs from a wild-type allele at a single nucleotide position and is present in the sample in low abundance amongst a large excess of the wild-type allele, the method comprising:

enriching the mutant allele in the sample wherein the enrichment is performed by:

providing an oligonucleotide that is complementary to one strand of the target nucleic acid at a concentration that is in molar excess to the target nucleic acid, wherein the oligonucleotide is attached with an affinity label and is perfectly matched at the single nucleotide position with the mutant allele and has a mismatch at the single nucleotide position with the wild-type allele;

providing conditions suitable for hybridization of the oligonucleotide to the target nucleic acid to generate duplex polynucleotides consisting of the oligonucleotide and one strand of either the mutant allele or the wild-type allele;

contacting the duplex polynucleotides with a mismatch intercalating compound that is capable of binding to only the duplex polynucleotides that contain a mismatch wherein said compound is further capable of catalyzing cleavage of one strand of the duplex polynucleotide at the mismatch site with light;

subjecting the duplex polynucleotides to light resulting in both cleaved and uncleaved duplex polynucleotides;

applying both cleaved and uncleaved duplex polynucleotides to an affinity matrix that recognizes and binds to the affinity label on the oligonucleotide;

providing conditions whereby only the cleaved duplex polynucleotide is denatured and removing the denatured single strand of the wild-type allele from the affinity matrix;

providing a buffer under conditions to denature the uncleaved polynucleotide duplex;

and collecting the buffer which contains one strand of the enriched mutant allele of the target nucleic acid;

amplifying the enriched mutant allele; and detecting the product of the enriched amplified mutant allele or the signal generated from the enriched amplified mutant allele.

7. The method of claim 6 wherein the mismatch intercalating compound is Rh(bpy)2(chrysi)3+, Rh(bpy)2(phzi)3+, or their analogs.

8. The method of claim 7 wherein the mutant allele is a mutant EGFR allele and the wild-type allele is a wild-type EGFR allele.

9. The method of claim 6 wherein the amplifying step is performed with allele-specific primers.

* * * * *

SEQUENCE LISTING

<160> NUMBER OF SEQ ID NOS: 5

<210> SEQ ID NO 1
<211> LENGTH: 30
<212> TYPE: DNA
<213> ORGANISM: Artificial Sequence
<220> FEATURE:
<223> OTHER INFORMATION: Wild-type sense oligonucleotide

<400> SEQUENCE: 1
cgtgcagctc atcacgcagc tcatgccctt                                          30

<210> SEQ ID NO 2
<211> LENGTH: 30
<212> TYPE: DNA
<213> ORGANISM: Artificial Sequence
<220> FEATURE:
<223> OTHER INFORMATION: Mutant sense oligonucleotide

<400> SEQUENCE: 2
cgtgcagctc atcatgcagc tcatgccctt                                          30

<210> SEQ ID NO 3
<211> LENGTH: 30
<212> TYPE: DNA
<213> ORGANISM: Artificial Sequence
<220> FEATURE:
<223> OTHER INFORMATION: Affinity-labeled antisense oligonucleotide
<220> FEATURE:
<221> NAME/KEY: misc_feature
<222> LOCATION: (30)..(30)
<223> OTHER INFORMATION: Biotin

<400> SEQUENCE: 3
aagggcatga gctgcatgat gagctgcacg                                          30

<210> SEQ ID NO 4
<211> LENGTH: 30
<212> TYPE: DNA
<213> ORGANISM: Artificial Sequence
<220> FEATURE:
<223> OTHER INFORMATION: Wild-type antisense oligonucleotide

<400> SEQUENCE: 4
aagggcatga gctgcgtgat gagctgcacg                                          30

<210> SEQ ID NO 5
<211> LENGTH: 30
<212> TYPE: DNA
<213> ORGANISM: Artificial Sequence
<220> FEATURE:
<223> OTHER INFORMATION: Mutant antisense oligonucleotide

<400> SEQUENCE: 5
aagggcatga gctgcatgat gagctgcacg                                          30